US010758900B2

(12) United States Patent
Saul

(10) Patent No.: US 10,758,900 B2
(45) Date of Patent: Sep. 1, 2020

(54) METHOD AND DEVICE FOR PREPARING AND EXTRACTING A BIOMOLECULE

(71) Applicant: David James Saul, Waiheke Island (NZ)

(72) Inventor: David James Saul, Waiheke Island (NZ)

( * ) Notice: Subject to any disclaimer, the term of this patent is extended or adjusted under 35 U.S.C. 154(b) by 0 days.

(21) Appl. No.: 15/556,199

(22) PCT Filed: Mar. 4, 2016

(86) PCT No.: PCT/NZ2016/050032
§ 371 (c)(1),
(2) Date: Sep. 6, 2017

(87) PCT Pub. No.: WO2016/144192
PCT Pub. Date: Sep. 15, 2016

(65) Prior Publication Data
US 2018/0043352 A1 Feb. 15, 2018

(30) Foreign Application Priority Data

Mar. 6, 2015 (NZ) ........................................ 705749

(51) Int. Cl.
*C12Q 1/686* (2018.01)
*B01L 3/00* (2006.01)
(Continued)

(52) U.S. Cl.
CPC .......... *B01L 3/502* (2013.01); *C12N 15/1003* (2013.01); *C12Q 1/686* (2013.01);
(Continued)

(58) Field of Classification Search
None
See application file for complete search history.

(56) References Cited

U.S. PATENT DOCUMENTS 5,188,260 A * 2/1993 Bettinger ............... B65D 25/00
174/DIG. 8
5,368,588 A 11/1994 Bettinger
(Continued)

FOREIGN PATENT DOCUMENTS

CN 201147695 Y 11/2008
EP 0 332 773 B1 9/1989
(Continued)

OTHER PUBLICATIONS

Communication, dated Jul. 13, 2018, issued by the European Patent Office in counterpart EP Application No. 16762042.6.
(Continued)

*Primary Examiner* — Young J Kim
(74) *Attorney, Agent, or Firm* — Sughrue Mion, PLLC

(57) ABSTRACT

The present invention provides an improved method and device for preparing, extracting, separating and/or purifying a biomolecule, for example, nucleic acid from a biological sample. The device comprises a heat-deformable material, such that an inner chamber adopts a second configuration having a chamber volume less than the chamber volume of a first configuration, thereby expelling at least a part of a processed sample through a second opening from the device, and thereby recovering the biomolecule-containing composition.

6 Claims, 6 Drawing Sheets

(51) Int. Cl.
*G01N 1/40* (2006.01)
*G01N 1/28* (2006.01)
*C12N 15/10* (2006.01)

(52) U.S. Cl.
CPC ........... *G01N 1/286* (2013.01); *G01N 1/4022* (2013.01); *B01L 2200/026* (2013.01); *B01L 2300/0832* (2013.01); *B01L 2300/12* (2013.01); *B01L 2300/123* (2013.01); *B01L 2400/0481* (2013.01); *B01L 2400/0661* (2013.01)

(56) References Cited

U.S. PATENT DOCUMENTS

| | | |
|---|---|---|
| 5,552,197 A | 9/1996 | Bettinger |
| 6,117,394 A | 9/2000 | Smith |
| 7,547,510 B2 | 6/2009 | Daniel et al. |
| 8,226,906 B2 | 7/2012 | Saul |
| 8,309,367 B2 | 11/2012 | Saul et al. |
| 8,597,878 B2 | 12/2013 | Hillebrand et al. |
| 2002/0187074 A1* | 12/2002 | O'Connor ............. B01F 5/0682 422/82.05 |
| 2010/0221814 A1 | 9/2010 | Asogawa et al. |
| 2011/0135546 A1 | 6/2011 | Kurowski et al. |
| 2013/0288257 A1 | 10/2013 | Wright |

FOREIGN PATENT DOCUMENTS

| | | |
|---|---|---|
| WO | 02/092844 A1 | 11/2002 |
| WO | 2005/122709 A2 | 12/2005 |
| WO | 2008/080932 A1 | 7/2008 |
| WO | 2010/093998 A2 | 8/2010 |

OTHER PUBLICATIONS

International Search Report for PCT/NZ2016/050032, dated May 19, 2016.
First Office Action dated May 23, 2019 issued by the China National Intellectual Property Administration in counterpart application No. 201680018094.2.
Communication dated Jul. 3, 2019 issued by the European Patent Office in counterpart application No. 16 762 042.6.

\* cited by examiner

METHOD AND DEVICE FOR PREPARING AND EXTRACTING A BIOMOLECULE

FIELD OF THE INVENTION

The present invention relates to an improved method and device for preparing, extracting, separating and/or purifying biological samples, for example a biomolecule such as nucleic acid from a biological sample.

BACKGROUND TO THE INVENTION

Methods and devices for the preparation of biomolecules such as nucleic acids from samples are known.

Nucleic acid-based diagnostic procedures in commercial and academic laboratories often require nucleic acid extractions from biological substances. Applications range from forensic DNA-fingerprinting to medical, agricultural and environmental monitoring. It is important that any nucleic acid extraction be free from contamination particularly where concentration of nucleic acid in the initial sample is very low or where contamination can lead to incorrect outcomes.

The polymerase chain reaction (PCR) has rapidly become one of the most widely used techniques in molecular biology. It is a rapid, inexpensive and simple means of producing relatively large numbers of copies of DNA molecules (via enzymatic amplification of a specific nucleic acid sequence of interest) from minute quantities of source material, even when the source nucleic acid is of relatively poor quality.

Although any protocol for template nucleic acid preparation is acceptable for PCR purposes, it is often best to use as few steps as possible for nucleic acid preparation in order to prevent yield reduction or accidental contamination with unwanted nucleic acid.

Known methods and devices for nucleic acid preparation typically involve processing the sample, for example, degrading tissue or lysing cells in the sample using physical homogenisation, enzymes, powerful detergents or chaotropic agents. The processed sample is then added to a column, sinter, beads or paramagnetic beads comprising a solid silica matrix that binds the nucleic acid. The silica matrix is washed, and the nucleic acid eluted in a low salt buffer to release the nucleic acid.

Additional purification or partial purification steps may be required to remove undesirable compounds co-extracted from the sample that interfere with downstream applications of the extracted nucleic acid, for example, contaminants that inhibit the PCR.

The minimisation of contamination is a significant factor in the purification of other biomolecules, such as peptides or proteins.

Existing methods and devices to extract or purify biomolecules are costly, time-consuming, require considerable handling by a skilled user, have a relatively high risk of contamination by the user, utilise toxic reagents, require complex equipment and/or reagents, and/or produce waste material having a significant environmental impact.

It is an object of the present invention to provide a method and device for preparing, extracting, purifying and/or separating a biomolecule that overcome one or more of the abovementioned disadvantages, or to at least provide the public with a useful choice.

SUMMARY OF THE INVENTION

In one aspect the invention relates to a method for preparing a biomolecule-containing composition, the method comprising the steps of a) providing a device comprising a body at least partially formed of a heat-deformable material, the body defining
 i. an inner chamber, wherein, in a first configuration, the inner chamber has a volume sufficient to receive a sample comprising a biomolecule,
 ii. a first opening located at one end of the device to receive said sample into the inner chamber, and
 iii. a second opening located at or towards the opposing end of the device, b) adding a sample comprising a biomolecule and one or more reagents to the inner chamber of said device, wherein at least one of the sample and the one or more reagents comprises a liquid;

c) maintaining the device at a first temperature and for a duration sufficient to allow the one or more reagents to modify one or more substances in the sample to form a processed sample comprising the biomolecule, and d) maintaining the device at a second temperature and for a duration sufficient to deform the heat-deformable material such that the inner chamber adopts a second configuration having a chamber volume less than the chamber volume of the first configuration, thereby expelling at least a part of the processed sample through the second opening from the device, and e) thereby recovering the biomolecule-containing composition.

In a second aspect the invention relates to a method for preparing a biomolecule-containing composition, the method comprising the steps of a) providing a device comprising
 i. an outer body,
 ii. a body housed at least partially within the outer body, the body at least partially formed of a heat-deformable material, and defining an inner chamber, wherein, in a first configuration, the inner chamber has a volume sufficient to receive a sample comprising a biomolecule,
 iii. a first opening located at one end of the device to receive said sample into the chamber, and
 iv. a second opening located at or towards the opposing end of the device, b) adding a sample comprising a biomolecule and one or more reagents to the inner chamber of said device, wherein at least one of the sample and the one or more reagents comprises a liquid;

c) maintaining the device at a first temperature and for a duration sufficient to allow the one or more reagents to modify one or more substances in the sample to form a processed sample comprising the biomolecule, and d) maintaining the device at a second temperature and for a duration sufficient to deform the heat-deformable material such that the inner chamber adopts a second configuration having a chamber volume less than the chamber volume of the first configuration, thereby expelling at least a part of the processed sample from the device, and e) thereby recovering the biomolecule-containing composition.

In a third aspect the invention relates to a method for preparing a biomolecule-containing composition, the method comprising the steps of a) providing a device comprising a body at least partially formed of a heat-deformable material, the body defining
 i. an inner chamber, wherein, in a first configuration, the chamber has a volume sufficient to receive a sample comprising a biomolecule, and wherein the inner chamber comprises one or more reagents,
  ii. a first opening located at one end of the device to receive said sample into the chamber, and
  iii. a second opening located at or towards the opposing end of the device,
b) adding a sample comprising a biomolecule into the inner chamber, wherein at least one of the sample and the one or more reagents comprises a liquid;
c) maintaining the device at a first temperature and for a duration sufficient to allow the one or more reagents to modify one or more substances in the sample to form a processed sample comprising the biomolecule, and
d) maintaining the device at a second temperature and for a duration sufficient to deform the heat-deformable material such that the inner chamber adopts a second configuration having a chamber volume less than the chamber volume of the first configuration, thereby expelling at least a part of the processed sample through the second opening from the device, and
e) thereby recovering the biomolecule-containing composition.

In a fourth aspect the invention relates to a method for preparing a biomolecule-containing composition, the method comprising the steps of
a) providing a device comprising
  i. an outer body,
  ii. a body housed at least partially within the outer body, the body at least partially formed of a heat-deformable material, and defining an inner chamber, wherein, in a first configuration, the inner chamber has a volume sufficient to receive a sample comprising a biomolecule, and wherein the inner chamber comprises one or more reagents,
  iii. a first opening located at one end of the device to receive said sample into the inner chamber, and
  iv. a second opening located at or towards the opposing end of the device,
b) adding a sample comprising a biomolecule into the inner chamber, wherein at least one of the sample and the one or more reagents comprises a liquid;
c) maintaining the device at a first temperature and for a duration sufficient to allow the one or more reagents to modify one or more substances in the sample to form a processed sample comprising the biomolecule, and
d) maintaining the device at a second temperature and for a duration sufficient to deform the heat-deformable material such that the inner chamber adopts a second configuration having a chamber volume less than the chamber volume of the first configuration, thereby expelling at least a part of the processed sample through the second opening from the device, and
e) thereby recovering the biomolecule-containing composition.

In a fifth aspect the invention provides a device for preparing a biomolecule-containing composition from a sample, the device comprising a body at least partially formed of a heat-deformable material, the body defining
a) an inner chamber, wherein, in a first configuration, the inner chamber has a volume sufficient to receive a sample comprising a biomolecule,
b) a first opening located at one end of the device to receive said sample into the inner chamber, and
c) a second opening located at or towards the opposing end of the device,
wherein, in use, upon application of heat, the heat-deformable material deforms such that the inner chamber adopts a second configuration having a chamber volume less than the chamber volume of the first configuration thereby expelling at least part of a processed sample comprising the biomolecule through the second opening from the device through the second opening.

In a sixth aspect the invention provides a device for preparing a biomolecule-containing composition from a sample, the device comprising
a) an outer body,
b) a body housed at least partially within the outer body, the body at least partially formed of a heat-deformable material, and defining an inner chamber, wherein, in a first configuration, the inner chamber has a volume sufficient to receive a sample comprising a biomolecule,
c) a first opening located at one end of the device to receive said sample into the inner chamber, and
d) a second opening located at or towards the opposing end of the device,
wherein, in use, upon application of heat, the heat-deformable material deforms such that the inner chamber adopts a second configuration having a chamber volume less than the chamber volume of the first configuration thereby expelling at least part of a processed sample comprising the biomolecule from the device through the second opening.

In one embodiment of the sixth aspect of the invention, the device comprises
a) an outer body formed substantially of a non-deformable material, the outer body defining an outer chamber, a first opening located at a first end of the device to receive said sample into the device and a second opening at the opposing end of the device,
b) a body housed at least partially within the outer body, the body at least partially formed of a heat-deformable material, and defining an inner chamber, wherein, in a first configuration, the inner chamber has a volume sufficient to receive a sample comprising a biomolecule,
  i) the body defining an opening located at the first end of the device to receive said sample into the inner chamber wherein the opposing end of the body is closed,
wherein, in use, upon application of heat, the heat-deformable material deforms such that the inner chamber adopts a second configuration having a chamber volume less than the chamber volume of the first configuration thereby expelling at least part of a processed sample comprising the biomolecule through the first opening of the inner chamber and into the outer chamber of the device.

In one embodiment the processed sample comprising the biomolecule is expelled from the device by gravity flow through the second opening. In another embodiment the biomolecule-containing composition the processed sample comprising the biomolecule is expelled from the device by centrifugation.

In another embodiment of the sixth aspect of the invention the device comprises
a) an outer body formed substantially of a non-deformable material, the outer body defining an outer chamber, a first opening located a first end of the device to receive said sample into the device and a second opening at the opposing end of the device, and
b) a body housed at least partially within the outer body, the body at least partially formed of a heat-deformable material, and defining an inner chamber, wherein, in a first configuration, the chamber has a volume sufficient to receive a sample comprising a biomolecule, i. the body defining a first opening located at the first end of the device to receive said sample into the chamber, and c) a valve located at the opposing end of the body, wherein, in use, upon application of heat, the heat-deformable material deforms such that the inner chamber adopts a second configuration having a chamber volume less than the chamber volume of the first configuration thereby expelling at least part of a processed sample comprising the biomolecule from the inner chamber through the valve and into the outer chamber of the device such that the sample is then expelled from the device through the second opening.

In a seventh aspect the invention provides a kit of parts for preparing a biomolecule-containing composition, the kit of parts comprising a) a device of the fifth or sixth aspect of the invention, and b) one or more reagents.

In one embodiment of the seventh aspect of the invention the kit of parts comprises one or more reagents provided in the inner chamber of the device. In an alternative embodiment the kit of parts comprises one or more reagents provided separately to the device.

Any one or more of the following embodiments may relate to any of the aspects described herein or any combination thereof.

In one embodiment the body is substantially formed of a heat-deformable material. In another embodiment the body is formed entirely of a heat-deformable material.

In various embodiments the heat-deformable material comprises polyolefin, a chlorinated polyolefin, poly-1,1-difluoroethene (PVDF), poly(1,1,2,2-tetrafluoroethylene) (PTEE), fluorinated ethylene propylene (FEP), poly(1-chloroethylene) (PVC), polychloroprene (neoprene), a fluoridated polymer, a silicon elastomer, or a combination of any two or more thereof.

In one embodiment the device comprises a cap configured to sealingly engage with the first opening.

In one embodiment the device comprises a valve. In one embodiment the valve is located at or adjacent to the opposing end of the body. In one embodiment the valve connects the inner and outer chambers of the device.

In one embodiment the valve is a one way valve. In various embodiments the valve is a thermostatic valve or a pressure-relief valve.

In various embodiments the valve comprises a soluble gel or a soluble wax. In one embodiment the soluble gel or soluble wax melts upon application of heat to the device.

In one embodiment the device comprises an outer body defining an outer chamber. In one embodiment the outer body comprises a first opening located at a first end of the device to receive said sample into the device. In a further embodiment the outer body comprises a second opening at the opposing end of the device. In one embodiment the body of the device is at least partially housed within the outer body. In another embodiment the body of the device is housed entirely within the outer body.

In one embodiment the outer body is formed substantially of a non-deformable material. In one embodiment the outer body is formed of a polypropylene, a polyethylene, or a polyvinyl chloride.

In one embodiment the outer body is formed of a material that substantially resists deformation at a temperature of less than about 150° C., 120° C., 100° C. or about 95° C. In one embodiment the outer body substantially resists deformation at the first and second temperatures.

In one embodiment the device comprises a body housed at least partially within the outer body, the body defining an opening located at the first end of the device to receive said sample into an inner chamber and to expel the sample from the device. In one embodiment the opposing end of the device is closed. In use, upon application of heat, the heat-deformable material deforms such that the inner chamber adopts a second configuration having a chamber volume less than the chamber volume of the first configuration thereby expelling substantially all of the processed sample comprising the biomolecule through the opening of the body and into an outer chamber of the device such that the sample is expelled from the device through the second opening in the outer body.

In one embodiment the inner chamber, in a second configuration, has a chamber volume of about 5, 10, 20, 25, 50, 75, 100, 120, 125, 140, 150, 160, 175, 180, 200, 225, 250, 300, 350, 400, 450, 500, 600, 700, 750, 800, or about 900 µL or about 1, 1.2, 1.25, 1.3, 1.4, 1.5, 1.6, 1.7, 1.75, 1.8, 1.9, 2, 2.25, 2.5, 3, 4, or about 5 mL, and useful ranges may be selected from between any of these values, for example from about 5 µL to about 5 mL, about 50 µL to about 2 mL, or about 100 µL to about 1.5 mL.

In one embodiment the opposing end of the body or the opposing end of the outer body is configured to engage with a collection tube. In various embodiments the opposing end of the body or the opposing end of the outer body is configured to engage with a collection tube by friction fit or a threading arrangement. In one embodiment the opposing end of the body or the opposing end of the outer body is configured to sealingly engage with a collection tube.

In one embodiment the device comprises one or more purification units comprising a material that binds or retains one or more contaminating substances. In one embodiment the one or more purification units are located at or adjacent to an opening of the body. For example, in one embodiment the one or more purification units is located at or adjacent to the second opening of the body. In one embodiment the one or more purification units is located at or adjacent to the valve.

In various embodiments the purification unit comprises a material selected from the group comprising activated charcoal, a chelating resin, an ion exchange resin, a desalting resin, a gel, a clay, a concentrating agent, and a water absorption material. For example, in various embodiments the purification unit comprises a cross-linked dextran gel, such as Sephadex®, Sephacryl® or Sepharose®, agarose, polyacrylamide, silica, silicon dioxide, zeolite, diatomaceous earth, coal-derived activated charcoal, plant-derived activated charcoal or paramagnetic silica.

In one embodiment the chamber comprises one or more reagents capable of modifying one or more substances in the sample. In one embodiment the chamber comprises one or more liquid reagents.

In one embodiment the device comprises a collection receptacle. In various embodiments the collection receptacle is a tube, tube strip, plate or tray.

In various embodiments, the device comprises an identification tag. In various examples, the identification tag is an optically-identifiable tag, a magnetically-identifiable tag, or a mechanical feature. In one example, the optically-identifiable tag is a scannable code such as a quick read (QR) code, a bar code, or a serial number. In one example, the magnetically-identifiable tag is a magnetic swipe strip. In one example, the identification tag is a radio frequency identification (RFID) tag. In one example, the mechanical feature comprises or includes a plurality of recesses or protrusions encoding identification data.

In one embodiment, the identification tag comprises sample identification data.

In one embodiment the method is a method of extracting a biomolecule from a sample. In another embodiment the method is a method of separating a biomolecule from a sample. In a further embodiment the method is a method of at least partially purifying a biomolecule.

In various embodiments the one or more reagents comprises an enzyme. In one embodiment the enzyme is a thermostable enzyme. In various embodiments the one or more reagents comprises a proteinase or a cell-wall degrading enzyme, or a proteinase and a cell-wall degrading enzyme. In various embodiments the one or more reagents comprises a serine protease, a metalloproteinase, a neutral proteinase, a threonine proteinase, an aspartate proteinase or a cysteine proteinase, or a combination of any two or more thereof. In various embodiments the one or more reagents comprises cellulase, hemicellulase, pectinase, glucouronidase, glucanase, chitinase, laminarinase, lyticase, lysozyme, subtilisin, proteinase K, trypsin, *Bacillus* sp. EA1 proteinase, thermolysin, caldolysin, a *Thermus* proteinase, or a combination of any two or more thereof.

In one specifically contemplated embodiment, the one or more reagents is or comprises EA1 proteinase (PCT international application PCT/NZ2002/00093, published on 21 Nov. 2002 as WO2002/092844, incorporated herein by reference in its entirety). For example, the device or kit of parts comprises EA1 proteinase.

In one embodiment the one or more reagents comprises one or more non-enzymatic reagents. In various embodiments the one or more reagents comprises potassium, sodium, magnesium or calcium ions, or a combination of any two or more thereof. In one embodiment the one or more reagents comprises one or more non-ionic surfactants selected from the group comprising a polyethylene oxide (Triton™), a co-polymer of ethylene oxide and propylene oxide, a polysorbate (Tween™), a fluorosurfactant (Capstone®), or a combination of any two or more thereof.

In one embodiment the sample comprises biological material. In various embodiments the biological material comprises whole blood, blood cells, serum, plasma, urine, faecal matter, cells, tissue, hair, saliva, sputum, cultured cells, vaginal fluid, semen, a swab, plant tissue, fungus, a surface wipe, or a microorganism.

In one embodiment the method comprises adding a sample comprising a liquid to the chamber of the device.

In another embodiment the method comprises adding a solid sample to the device. In another embodiment the method comprises adding a solid sample bound to a sample-holding matrix to the device. In various embodiments the sample-holding matrix is in the form of a swab, a storage card, a preservation matrix, for example DNAStable®, or a collection device.

In one embodiment the method comprises adding a solid sample or a solid sample bound to a sample-holding matrix and one or more liquid reagents to the chamber of the device. In another embodiment the chamber comprises one or more liquid reagents and the method comprises adding a solid sample or a solid sample bound to a sample-holding matrix to the chamber of the device.

In various embodiments the biomolecule is a nucleic acid, a peptide, a saccharide, a lipid or a protein.

In one embodiment the second temperature is sufficient to inactivate the one or more reagents.

In one embodiment the method further comprises an additional heating step between step c) and step d), or after step d), the additional heating step comprising maintaining the device at a temperature and for a duration sufficient to inactivate the one or more reagents.

In one embodiment the method comprises maintaining the device at a first temperature at which the inner chamber is not substantially deformed.

In various embodiments the method comprises maintaining the device at a first temperature of about 20, 25, 30, 35, 40, 45, 50, 55, 60, 65, 70, 72, 75, 80 or about 85° C., and useful ranges may be selected from between any two or these values, for example, from about 40 to about 85° C., about 65 to about 80° C., or from about 65 to about 75° C.

In various embodiments the method comprises maintaining the device at a first temperature for a period of about 30 seconds, about 1, 1.5, 2, 2.5, 3, 4, 5, 7.5, 8, 9, 10, 15, 20, 25, 30, 40, 45, 50, or about 60 minutes, or about 2, 3, 4, 5, 6, 8, 9 or 12 hours and useful ranges may be selected from between any two or these values, for example, from about 30 seconds to about 12 hours, about 30 seconds to about 10 minutes, or from about 1 minute to about 5 minutes.

In a particularly contemplated embodiment the method comprises maintaining the device at a first temperature and for a duration sufficient to allow a proteinase to lyse substantially all of the cells in the sample.

In one embodiment the method comprises maintaining the device at a second temperature of greater than about 60, 65, 70, 75, 80, 85, 90, 95, 99, 100, 105, 110, 115 or about 120° C., and useful ranges may be selected from between any two or these values, for example, from about 60 to about 120° C., about 80 to about 100° C., or from about 85 to about 99° C.

In various embodiments the method comprises maintaining the device at a second temperature for a period of about 15, 20, or about 30 seconds, about 1, 1.5, 2, 2.5, 3, 4, 5, 7.5, 8, 9, 10, 15, 20, 25, 30, 40, 45, 50, or about 60 minutes, and useful ranges may be selected from between any two or these values, for example, from about 15 seconds to about 60 minutes, about 15 seconds to about 10 minutes, or from about 30 seconds to about 5 minutes.

In various embodiments the method further comprises an additional heating step before step c). In one embodiment the additional heating step comprises maintaining the device at a temperature and for a duration sufficient to modify one or more substances in the sample.

In one embodiment the method comprises the steps of
a) providing a device of the invention,
b) adding a sample comprising a biomolecule and two or more reagents to the inner chamber of said device, wherein at least one of the sample and the one or more reagents comprises a liquid;
c) maintaining the device at a first reaction temperature and for a duration sufficient to allow a first reagent to modify one or more substances in the sample, wherein at the first temperature, the inner chamber is not substantially deformed;
d) maintaining the device at a second reaction temperature and for a duration sufficient to allow a second reagent to modify one or more substances in the sample, wherein at the second temperature, the inner chamber is not substantially deformed;
e) maintaining the device at a second temperature and for a duration sufficient to deform the heat-deformable material such that the inner chamber adopts a second configuration having a chamber volume less than the chamber volume of the first configuration, thereby expelling at least a part of the processed sample comprising the biomolecule through the second opening from the device, and
f) thereby recovering the biomolecule-containing composition.

In one embodiment the method comprises maintaining the device at a first reaction temperature and for a duration sufficient to allow a mesophilic enzyme to modify one or more substances in the sample, and maintaining the device at a second reaction temperature sufficient to allow a thermophilic enzyme to modify one or more substances in the sample.

In various embodiments the method comprises maintaining the device at a first reaction temperature of about 10, 15, 20, 25, 30, 35, 40, 45, 50, 55, 60, 65, or about 70° C., and useful ranges may be selected from between any two or these values, for example, from about 15 to about 70° C., about 15 to about 60° C., or from about 15 to about 50° C.

In various embodiments the method comprises maintaining the device at a second reaction temperature of about 40, 45, 50, 55, 60, 65, 70, 75, 80, or about 85° C., and useful ranges may be selected from between any two or these values, for example, from about 40 to about 85° C., about 45 to about 85° C., or from about 50 to about 85° C.

In one embodiment the method comprises maintaining the device at a second temperature such that substantially all of the processed sample is expelled from through the device.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

BRIEF DESCRIPTION OF THE DRAWINGS

The invention will now be described by way of example only and with reference to the drawings in which.

DETAILED DESCRIPTION OF THE INVENTION

Figure 1:
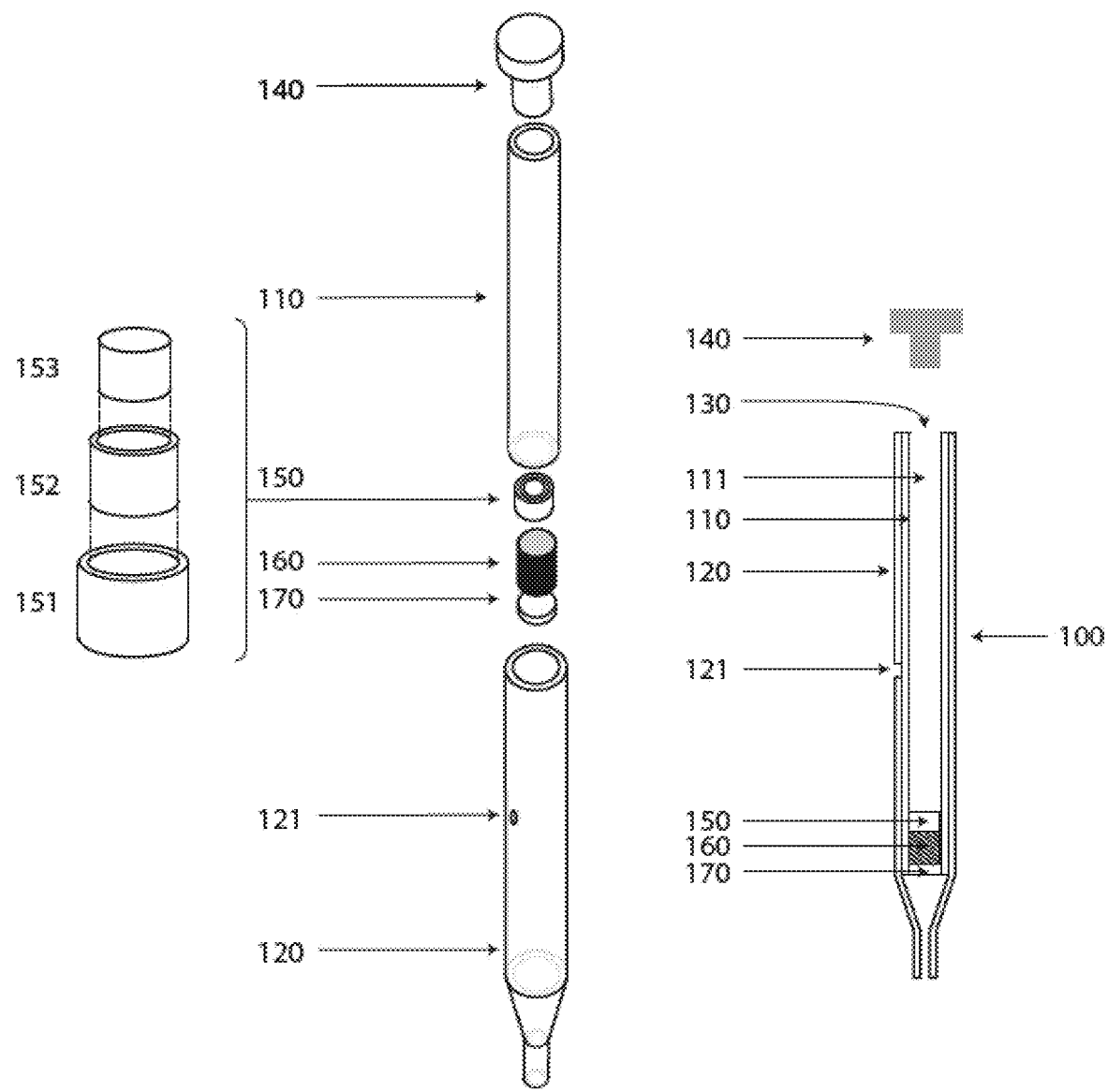
FIG. 1 is an exploded view (left) and a schematic (right) depicting a device of the invention.

The present invention relates to a device and method for preparing, separating, extracting or purifying a biomolecule from a sample. The device comprises a body defining an inner chamber, the body at least partially formed of a heat-deformable material, wherein the body deforms upon application of heat to drive a composition comprising the biomolecule from the device.

Embodiments of the methods and devices of the invention have numerous advantages, including but not limited to
- efficient and rapid separation, extraction and/or purification of biomolecules,
- suitability for processing a diverse range of samples, for example, solid tissue, swabs, liquid samples such as blood and saliva, and cultured cells,
- the device is simple and low-cost to maintain and manufacture,
- the device has no mechanical moving parts,
- the device is portable,
- the method is simple and fast,
- the method requires no complex equipment,
- reduced handling of the sample by the user thereby reducing opportunity for accidental contamination of the extracted biomolecule, or
- suitable for use in a low-resource environment.

1. Definitions

The term "and/or" can mean "and" or "or".

The term "comprising" as used in this specification means "consisting at least in part of". When interpreting statements in this specification which include that term, the features, prefaced by that term in each statement, all need to be present but other features can also be present. Related terms such as "comprise" and "comprised" are to be interpreted in the same manner.

The term "deformable" as used in this specification to describe a body means "susceptible to contracting or shrinking upon application of pressure or stress". Related terms such as "deform" and "deforms" are to be interpreted in the same manner. The term "heat-deformable" as used herein to describe a body means that upon application of heat the body contracts or shrinks. For example, the body may deform upon application of heat at a temperature of greater than about 60, 65, 70, 75, 80, 85, 90, 95, 100, 105, 110, 115 or about 120° C. The term "non-deformable" as used herein to describe a body means that upon application of heat the body does not substantially contract or shrink.

The term "nucleic acid" as used in this specification refers to a single- or double-stranded polymer of deoxyribonucleotides (DNA), ribonucleotide bases (RNA) or known analogues of natural nucleotides, or mixtures thereof. The term includes reference to synthetic, modified or tagged nucleotides.

The term "(s)" following a noun contemplates the singular or plural form, or both.

The term "sample" as used in this specification refers to any material from which a biomolecule is to be prepared, extracted, purified or separated. The sample may comprise a natural or biological sample, for example, a sample of urine, whole blood, blood cells, serum, plasma, urine, faecal matter, cells, tissue, saliva, sputum, cultured cells, vaginal fluid, a swab, plant tissue, fungus, or a microorganism. The sample may comprise a natural or biological sample such as those listed above that is bound to a sample-holding matrix, for example, a swab or storage card. In some cases the sample-holding matrix will have been used to obtain the sample from a source (for example, a buccal swab) and is able to be added directly to the device of the invention for extraction, purification, separation or preparation of the biomolecule from the sample.

2. Device and Method of the Invention

Device 100 of the present invention as shown in FIG. 1 comprises a body 110 defining an inner chamber 111. In an exemplary embodiment body 110 is in the form of a tube.

Body 110 is at least partially formed from a heat-deformable material such as polyolefin. Other examples of suitable heat-deformable materials include polymers such as poly-1,1-difluoroethene (PVDF), poly(1,1,2,2-tetrafluoroethylene) (PTFE), fluorinated ethylene propylene (FEP), poly(1-chloroethylene) (PVC), polychloroprene (neoprene), other fluoridated polymers or silicon elastomers. Other suitable heat-deformable materials, such as those commonly used in the art to form heat-shrink tubing, will be apparent to those skilled in the art.

In a particularly preferred embodiment, body 110 is housed within an outer body 120. In one embodiment outer body 120 is in the form of a tube.

In one embodiment outer body 120 is formed from a non-deformable, rigid material, for example, polypropylene, a polyethylene, or a polyvinyl chloride. Other suitable materials will be apparent to those skilled in the art.

In one embodiment outer body 120 defines one or more apertures 121 that allow body 110 to deform without negative pressure building inside outer body 120.

In one embodiment outer body 120 comprises an opening 122 through which a composition comprising the biomolecule is expelled from the device.

In one embodiment outer body 120 is configured to sealingly engage with a collection tube (not shown). For example, outer body 120 is configured to engage with a collection tube by friction fit or by a threading arrangement.

The device may be configured to engage with many standard laboratory collection tubes, tube strips or plates, for example, Eppendorf® tubes, PCR tubes, Luer-lok tubes, or custom vessels for specific diagnostic apparatus.

In an alternative embodiment the end of outer body 120 is sealed. In this embodiment the outer body functions as a collection tube for the composition comprising the biomolecule.

The device comprises an opening 130 to receive a sample into the inner chamber 111.

In one embodiment the device comprises a cap 140 that sealingly engages opening 130.

In one embodiment the device comprises a valve 150 located at the base of the body. For example, in one embodiment valve 150 comprises a thermostatic valve such as that shown in FIG. 1. In this embodiment the thermostatic valve is a simple, low-cost assembly comprising an outer rigid support tube 151, a short length of heat-deformable tubing 152 friction fitted inside the outer support tube 151 and a compressible, waterproof foam 153 that seals the valve. The outer diameter of outer support tube 151 is approximately equal to the inner diameter of body 110. The heat-deformable tubing 152 is preferably formed of the same material as body 110.

In another embodiment valve 150 is a pressure-burst valve.

In an alternative embodiment the device comprises a meltable or soluble gel or wax at the base of the body. In this embodiment, upon application of heat to the device, the gel or wax melts or dissolves allowing passage of the sample from the inner chamber.

In one embodiment the device comprises a purification unit 160 comprising a material that binds or retains one or more unwanted or contaminating substances present in the sample or generated by modification of one or more substances present in the sample. The material may bind or retain substances that are deleterious to downstream applications of the biomolecule. For example, the material may bind or retain salts including potassium, calcium, magnesium or sodium salts, detergents including sodium dodecyl sulfate, peptides or peptide complexes such as IgG, or haem. In one embodiment the purification material is insoluble.

In various embodiments the purification unit comprises a material selected from the group comprising activated charcoal, a chelating resin, an ion exchange resin, a desalting resin, a gel, a clay, a concentrating agent, and a water absorption material. For example, in various embodiments the purification unit comprises a cross-linked dextran gel, such as Sephadex®, Sephacryl® or Sepharose®, agarose, polyacrylamide, silica, silicon dioxide, zeolite, diatomaceous earth, coal-derived activated charcoal, plant-derived activated charcoal or paramagnetic silica.

In one exemplary embodiment purification unit 160 is located adjacent to the valve. In one embodiment the device comprises one or more purification units arranged in series. In one embodiment the purification material is in the form of a pellet.

In one embodiment the device comprises a frit 170 configured to prevent the purification material from leaking out of the device. In various embodiments frit 170 comprises filter paper, mesh, or other porous, inert materials.

In one embodiment valve 150, purification unit 160 or frit 170 are integral with body 110. In one embodiment valve 150 and purification unit 160 are integral with body 110. In a further embodiment valve 150, purification unit 160 and frit 170 are integral with body 110.

In one embodiment the device is configured to have dimensions suitable to fit firmly into the wells or channels of standard laboratory heating equipment, for example, the wells or channels of commercially available heat blocks or PCR thermal cyclers.

In one embodiment the one or more reagents are provided within inner chamber 111 of the device. The reagents may be provided in inner chamber 111 in the form of a liquid or solution, or in the form of a solid that is dissolved upon addition of a liquid sample or buffer to the inner chamber.

Figure 2:
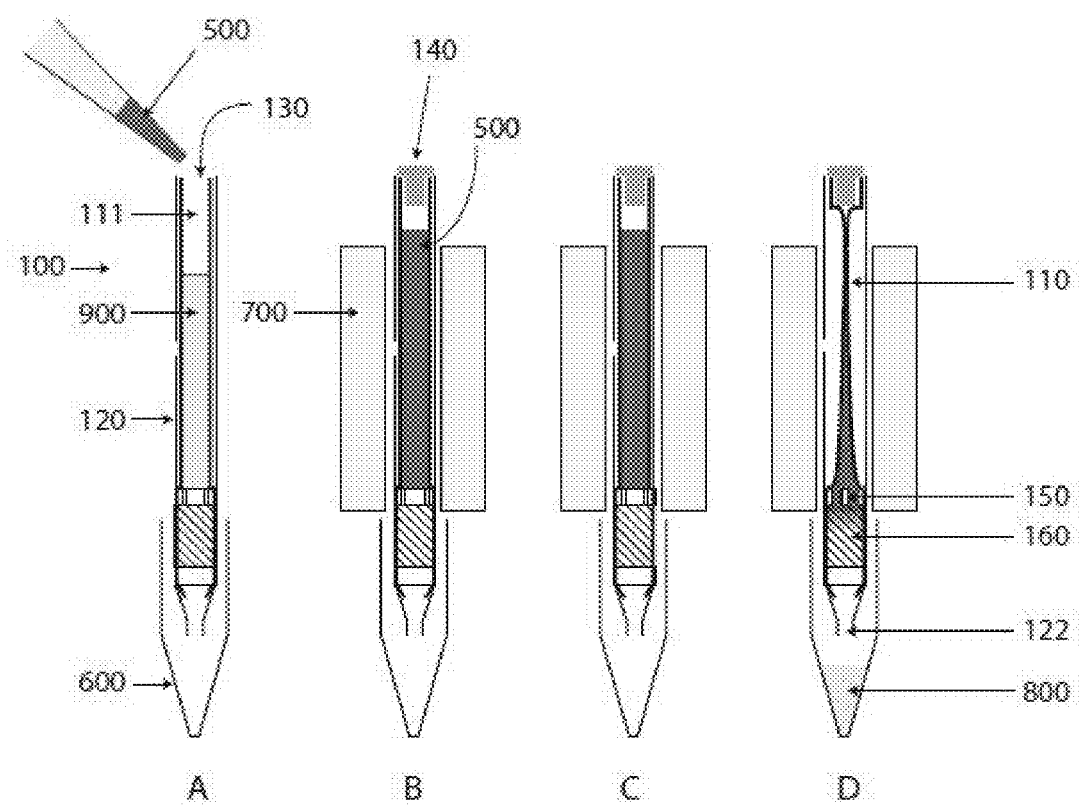
FIG. 2 is a schematic depicting a method of the invention.

Referring to the process diagram shown in FIG. 2, one embodiment of the method of the invention may comprise the following steps.

A device of the invention 100 is provided. A sample 500 is added to inner chamber 111 of body 110 as shown in part A of FIG. 2. In one embodiment the sample is in the form of a liquid and is added through opening 130 of the device into the inner chamber 111 by pipetting.

In one embodiment the device is supplied comprising one or more of the reagents 900 required to modify one or more substances in sample 500 as shown in part A of FIG. 2. In an alternative embodiment the reagents are added to inner chamber 111 simultaneously or sequentially with sample 500. For example, the one or more reagents may be pre-mixed with the sample before addition to the device.

In one embodiment the user fits a collection tube 600 to the device. In an alternative embodiment the collection tube is integral with the device.

Cap 140 is inserted into the device to seal opening 130, as shown in part B of FIG. 2. The sample and reagents may be mixed. Device 100 is inserted into the channel or well of a heating device 700.

Preferably, the heating device for use in the method of the invention comprises a temperature controller programmable to maintain one or more temperatures for defined periods. The device may comprise multiple channels or wells for simultaneous processing of multiple samples. Such devices are readily available, and are common equipment in research and commercial laboratories.

Device 100 is maintained at a first temperature and for a period of time sufficient to modify one or more substances present in sample 500 to form a processed sample comprising the biomolecule as shown in part C of FIG. 2. In one embodiment body 110 is not substantially deformed at the first temperature. In a preferred embodiment the device is heated at a temperature of less than about 80° C. for a period of from about 30 seconds to about 12 hours.

Device 100 is maintained at a second temperature and for a period of time sufficient to substantially deform body 110 as shown in part D of FIG. 2. Body 110 is deformed such that the volume of inner chamber 111 is substantially reduced creating a positive pressure within body 120. Simultaneously, heat-deformable tubing 152 within valve 150 contracts, compressing foam 153 thereby opening valve 150. Substantially all of the processed sample comprising the biomolecule is thereby expelled from inner chamber 111, through valve 150 and purification unit 160 to exit the device through opening 122.

In one embodiment the diameter of body 110 is reduced by about half relative to the diameter of the non-deformed body.

In one exemplary embodiment the device is heated at a second temperature of from about 85 to about 100° C. for a period of from about 15 seconds to about 2 minutes.

In one embodiment one or more of the reagents 900 are inactivated at the second temperature.

Processed sample 800 comprising the biomolecule is collected in collection tube 600.

In an embodiment where the collection tube is separate from the device, the collection tube comprising the processed sample comprising the biomolecule is separated from the device. In an alternative embodiment where the collection tube is integral with the device, the extract comprising the biomolecule may be recovered from the device by removing cap 140, then removing body 110, valve 150 and purification unit 160 from the device. The device is optionally re-sealed with cap 140 and may act as a storage tube for the processed sample comprising the biomolecule.

Figure 3:
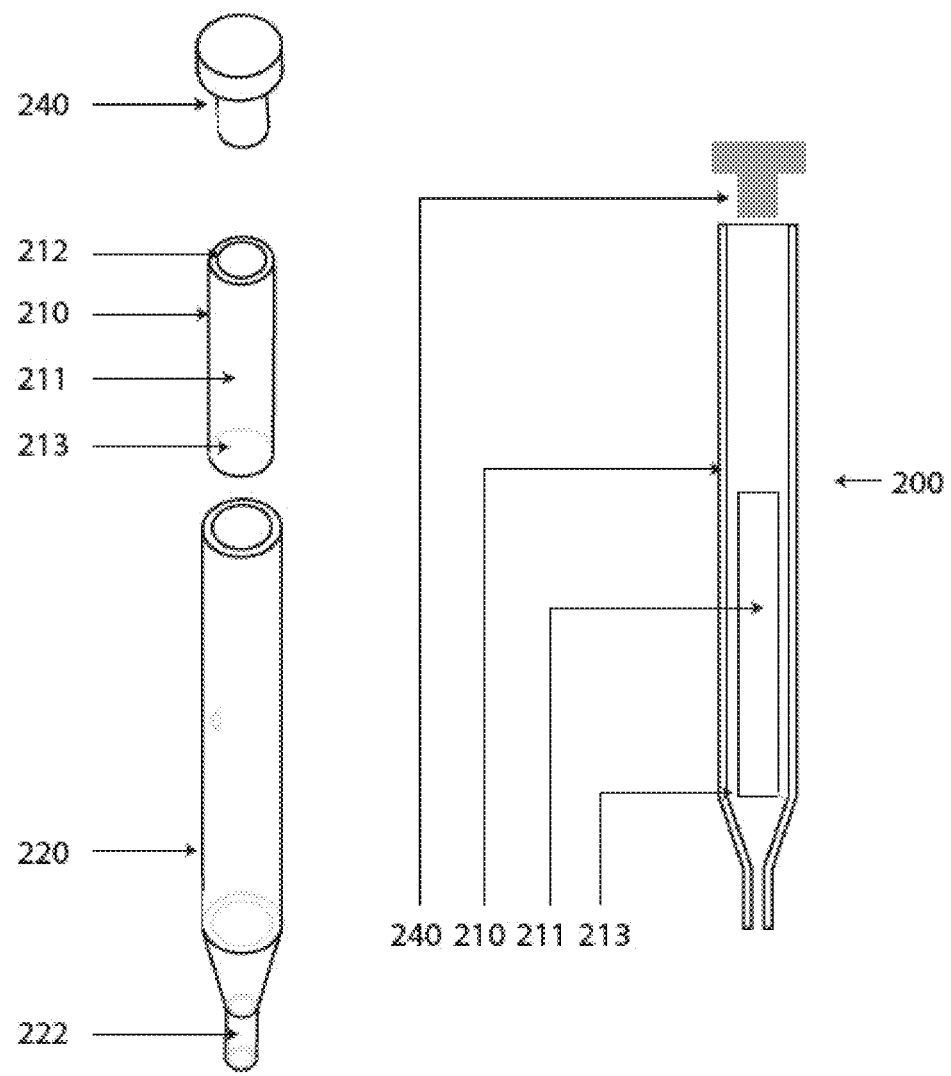
FIG. 3 is an exploded view (left) and a schematic (right) depicting a device of the invention.

An alternative embodiment of the device of the invention is shown in FIG. 3.

Device 200 comprises a body 210 defining an inner chamber 211. The body 210 is at least partially formed from a heat-deformable material as described above. The body 210 comprises an opening 212 at one end to receive a sample into the inner chamber 211. The opposing end 213 of body 210 is sealed.

After adding a sample to inner chamber 211, the device may be sealed by cap 240.

The body 210 is housed within an outer body 220. Outer body 220 is formed from a non-deformable, rigid material as described above. Outer body 220 comprises an opening 212 to receive a sample into the device and into inner chamber 211. Outer body 220 further comprises an opening 122 to allow liquids to be expelled from the device.

Body 210 fits within outer body 220 such that the rim 212 of body 210 is below opening 212. Furthermore, body 210 is located within outer body 220 such that liquid expelled from opening 212 flows out of inner chamber 221, and, by gravity, flows down the sides of body 210 and is expelled from the device through opening 222.

Figure 4:
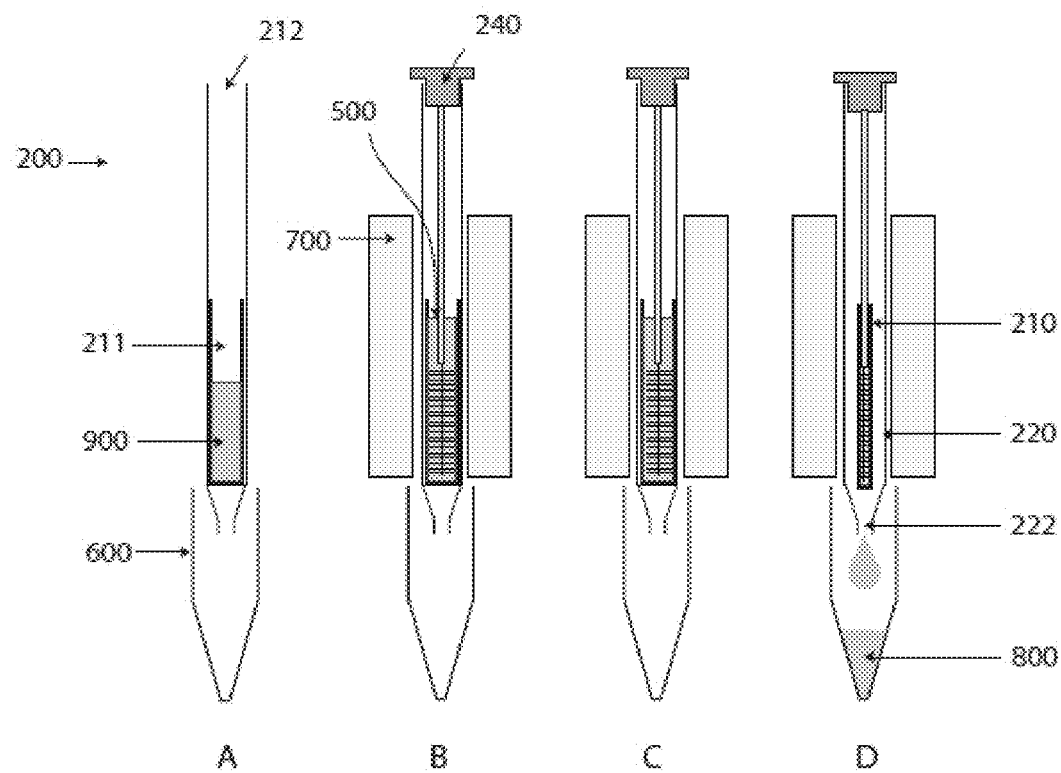
FIG. 4 is a schematic depicting a method of the invention.

Referring to the process diagram shown in FIG. 4, a method of the invention utilising the device shown in FIG. 3 may comprise the following steps. The method is the same as that described above for device 100, except for the variations described below.

A device 200 of the invention is provided as shown in part A of FIG. 4.

The device may be supplied comprising one or more liquid reagents 900 in inner chamber 211, or the one or more reagents may be added to inner chamber 211 of body 210 as described above.

A sample 500 is added to inner chamber 211 of body 210 as shown in part B of FIG. 4. In one embodiment the sample is in the form of cells or tissue bound to a swab.

A collection tube 600 may be fitted to the device as described above.

Cap 240 is inserted into the device to seal opening 212, as shown in part B of FIG. 4. The sample and reagents may be mixed to disperse the tissue or cells throughout the liquid reagents. Device 200 is inserted into the channel or well of a heating device 700.

Device 200 is maintained at a first temperature and for a period of time sufficient to modify one or more substances present in sample 500 to form a processed sample comprising the biomolecule as shown in part C of FIG. 4. Suitable conditions for this step are as described above for device 100.

Device 200 is heated at a second temperature and for a period of time sufficient to substantially deform body 210 as shown in part D of FIG. 4. Deformation of the body substantially reduces the volume of inner chamber 211 forcing substantially all of the processed sample comprising the biomolecule 800 from inner chamber 211 through opening 212 and into outer body 220. Processed sample 800 flows down the sides of body 210 by action of gravity and is expelled from the device and through opening 222.

3. Applications of the Device and Method of the Invention

The device and methods of the invention are suitable for preparing, extracting, purifying or separating biomolecules from a wide range of samples.

In a particularly preferred embodiment the sample is a biological sample.

In one embodiment the sample is derived from a human or a non-human animal subject. Examples of samples obtained from humans or non-human animals that are suitable for use in the invention are described above.

In one embodiment the sample is obtained from a microorganism. In various embodiments the sample comprises bacteria, yeast, fungi, endophytes or spores.

In one embodiment the sample is derived from plant tissue. In various embodiments the sample is derived from the leaves, stems, roots, flowers, seeds, sap, bark, pollen or nectar of a plant.

In one embodiment the sample is a crude or unprocessed sample. For example, the sample may be a crude sample obtained from a subject or source and applied directly to the device without any processing or purification steps undertaken.

In one embodiment the sample comprises a partially purified preparation comprising a biomolecule. For example, in various embodiments the sample comprises a cell lysate, partially degraded tissue, or a sample that has undergone one or more partial purification steps. In one embodiment the method of the invention is used to remove one or more residual contaminants or undesirable substances from a sample comprising a biomolecule to obtain a composition comprising a substantially pure biomolecule.

In various embodiments the one or more reagents comprises an enzyme. In various embodiments the enzyme is selected from the group comprising a thermostable enzyme, a thermophilic enzyme, a mesophilic enzyme, a proteolytic enzyme, an alkaline proteinase, a serine protease, a metalloproteinase, a neutral proteinase, a threonine proteinase, an aspartate proteinase, a cysteine proteinase, a cell-wall degrading enzyme, and a combination of any two or more thereof. In various embodiments the one or more reagents comprises cellulase, hemicellulase, pectinase, glucouronidase, glucanase, chitinase, laminarinase, lyticase, lysozyme, subtilisin, proteinase K, trypsin, *Bacillus* sp. EA1 proteinase, thermolysin, caldolysin, a pectate lyase, polygalacturonase, lysozyme, a lysin, a lytic enzyme, a *Thermus* proteinase, or a combination of any two or more thereof.

In one exemplary embodiment the one or more reagents comprises a thermostable proteinase derived from a thermophilic or mesophilic microorganism. For example, in one embodiment the one or more reagents comprises a thermostable proteinase derived from a thermophilic *Bacillus* species.

In particularly contemplated embodiments the one or more reagents comprises a thermostable proteinase derived from *Bacillus* sp. strain EA1 or from *Bacillus* sp. strain Ak1. These enzymes are described in detail in U.S. Pat. No. 7,546,510, which is hereby incorporated by reference.

In one embodiment the one or more reagents comprises two or more enzymes. For example, in one embodiment the one or more reagents comprises a mesophilic enzyme and a thermophilic enzyme.

In one embodiment the one or more reagents comprises one or more non-enzymatic reagents. In one embodiment the one or more reagents comprises one or more cations selected from the group comprising potassium, sodium, magnesium and calcium ions. In one embodiment the one or more reagents comprises one or more non-ionic surfactants selected from the group comprising a polyethylene oxide (Triton™), a co-polymer of ethylene oxide and propylene oxide, a fluorosurfactant, a polysorbate (Tween™), or a combination of any two or more thereof.

In one embodiment, for example, a method of extracting one or more biomolecules from a sample comprising cells, the method comprises maintaining the device at a first temperature for a duration sufficient to
  a) lyse at least a portion of the cells present in the sample, or
  b) at least partially digest one or more proteins present in the sample, or
  c) both a) and b).

In one embodiment maintaining the device at the second temperature sequentially or simultaneously induces inactivation of the one or more reagents and deformation of the body. For example, in one embodiment wherein the one or more reagents comprises an enzyme, maintaining the device at the second temperature induces inactivation or autolysis of the enzyme.

In an alternative embodiment the method further comprises an additional heating step between step c) and step d), or after step d). In one embodiment the additional heating step comprising maintaining the device at a temperature and for a duration sufficient to inactivate the one or more reagents.

In another embodiment the one or more reagents comprises a first reagent and a second reagent wherein step c) of the method comprises maintaining the device at a first reaction temperature and for a duration sufficient to allow the first reagent to modify one or more substances in the sample. In this embodiment the additional heating step further comprises maintaining the device at a second reaction temperature and for a duration sufficient to allow the second reagent to modify one or more substances in the sample.

In one embodiment the first reagent is a mesophilic enzyme and the second reagent is a thermophilic enzyme.

It will be appreciated that where the additional heating step is between step c) and step d), the temperature is not sufficient to substantially deform the heat-deformable material. It will be further appreciated that where the additional heating step is after step d), the temperature may or may not be a temperature at which the heat-deformable material is substantially deformed.

It is desirable that the first and second temperatures are temperatures at which deleterious enzymes or substances present in the sample, for example, DNases released from lysed cells, are not active.

It will be appreciated by a person skilled in the art that different reagents will be active at different temperatures, and that the first temperature can be adjusted to a temperature at which sufficient activity for the particular reagent used is achieved.

It will be further appreciated that the second temperature may be adjusted dependent on the heat-deformable material used, the temperature at which the one or more reagents is active, or a combination of both these considerations.

In a particularly preferred embodiment the method comprises extracting nucleic acid from a sample comprising cells. In this embodiment the one or more reagents comprises EA1 protease. In this embodiment the method comprises the steps of maintaining the device at a temperature of from about 70° C. to about 75° C. for a duration of about 2 minutes to about 10 minutes, and maintaining the device at a temperature of from about 90° C. to about 95° C. for a duration of about 1 minute to about 3 minutes. In this embodiment, low temperature polyolefin has been found to be a suitable heat-deformable material.

It will be appreciated by those skilled in the art that the device and methods of the invention are suitable for the preparation, extraction, separation, or purification of various types of biomolecules from a range of sample types for many medical, laboratory, horticultural, veterinary, agricultural, environmental, forensic or diagnostic applications.

The method and device of the invention are useful for applications where the sample comprises minute quantities of the biomolecule, where the biomolecule is of relatively poor quality, or where it is critical that the composition comprising the biomolecule comprises low or no contaminants.

The method and device of the invention are particularly useful for extracting or purifying nucleic acids, such as deoxyribose nucleic acid (DNA) or ribonucleic acid (RNA)

for a variety of molecular biology applications. For example, the method and device of the invention may be used to produce a composition comprising nucleic acid extracted from a sample that is suitable for immediate use for a polymerase chain reaction (PCR), reverse transcriptase PCR (RT-PCR), quantitative PCR (qPCR or qRT-PCR), forensic DNA fingerprinting, fluorescence-based detection, chip-based hybridisation detection, evaporation enrichment, DNA sequencing, RNA sequencing, molecular beacons, electrophoresis, direct electronic detection or nanopore analysis.

The method and device of the invention are suitable for the preparation of nucleic acids for applications where the concentration of nucleic acid in the sample may be very low and where contamination may lead to an incorrect analysis of the nucleic acid.

An advantage of the invention is that the device is portable and the method may be carried out using simple equipment. Therefore, the method and device of the invention are particularly suited to point-of-care and point-of-use applications. For example, the device may be used in the field or at the bedside to obtain rapid extraction or purification of biomolecules from sample to reduce the potential for contamination or degradation of the biomolecule.

The invention consists in the foregoing and also envisages constructions of which the following gives examples only and in no way limit the scope thereof.

EXAMPLES

Example 1

This example investigates extraction of nucleic acid from a sample using a device and method of the invention.
1. Extraction A device as shown in FIG. 3 comprising an inner heat-shrink tube having a closed end was used.

200 µL buffer comprising 5 mM Tris (pH 8.3 at 20° C.), 0.5% Triton X-100 and 4 µL prepGEM enzyme (ZyGEM Corporation Ltd, New Zealand) was added into the heat-shrink tube of the device.

A buccal swab was taken by rubbing the inside cheek of an individual vigorously for 30 seconds. The swab was inserted into the heat-deformable tube in the device and rotated to mix the reagents and to dislodge bubbles. With the swab inserted in the device, the level of the liquid in the heat-shrink tube was approximately 5 mm below the open end of the tube through which the swab was inserted.

The device was heated for 5 minutes at 75° C. and then for 2 minutes at 95° C.

After 30 seconds at the higher temperature, liquid flowed from the device and was collected in a tube. Approximately 150 µL of the extract was recovered.
2. Quantitative PCR A reaction mix comprising 12.5 µL PerfeCTa SYBR Green FastMix (Quanta BioSciences, USA), 1 µL each of the following two primers that amplify a sequence of the human glyceraldehyde-3-phosphate dehydrogenase (GAPDH) gene at 10 µM (Forward: TCTCCTC-CGATTTCAACAGTGA, Reverse: GGTCGTT-GAGGGCAATGC, product size=72 bp), and 6.5 µl water was prepared per sample.

Five µL samples of the extract or standards comprising known amounts of human DNA were added to the reaction mix.

Quantitative PCR to amplify nucleic acid in the extract or standards was conducted using an Applied Biosystems 7300 Real Time PCR machine. Cycling conditions were an initial activation at 94° C. for 3 minutes followed by 40 cycles of; 94° C. for 3 sec, 60° C. for 30 sec.

Figure 5:
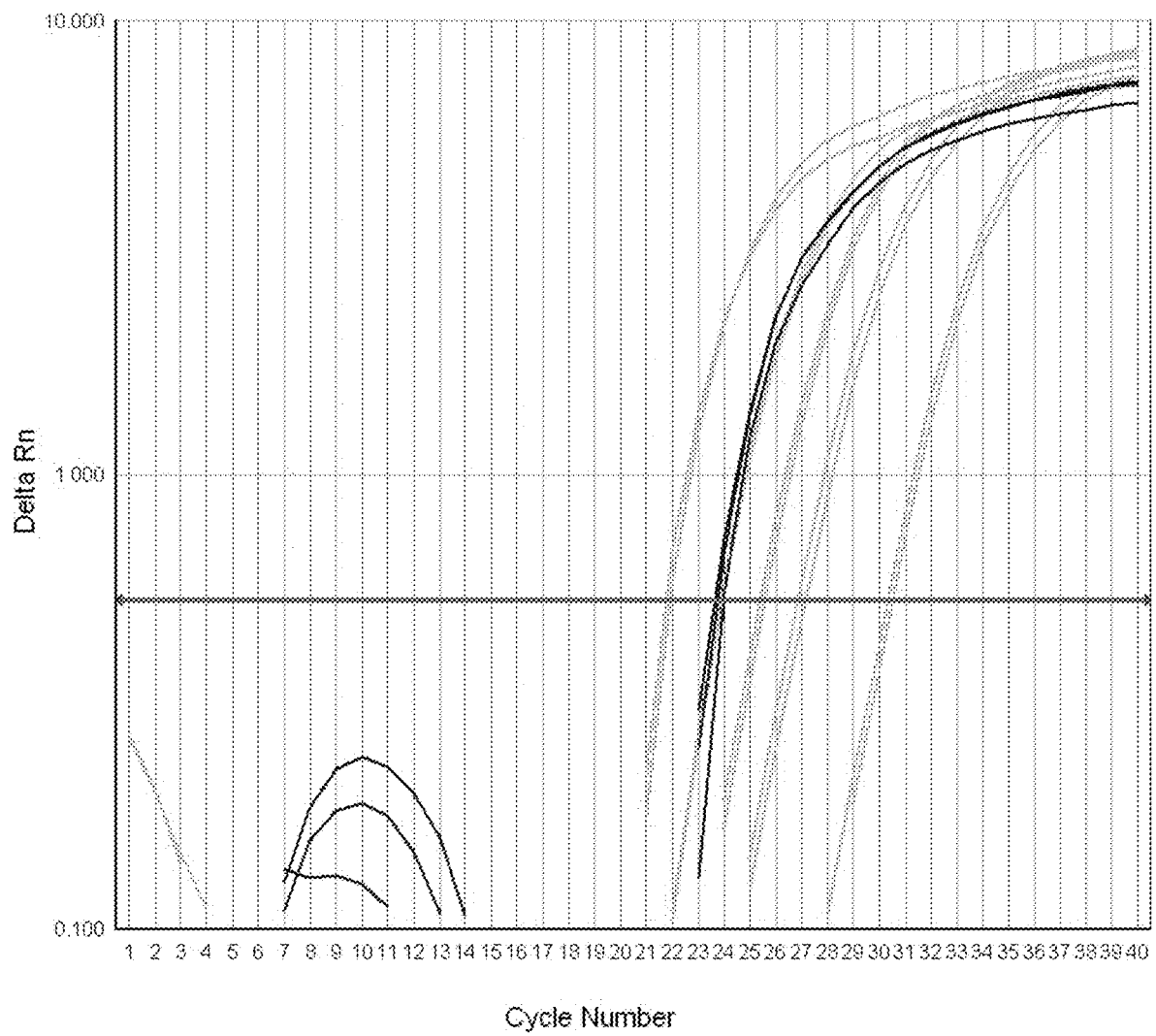
FIG. 5 shows the results of quantitative PCR of an extract obtained from a buccal swab sample using a method and device of the invention. The black plots show amplification of samples of the extract. The grey plots, from left to right, show amplification of standards comprising: 5.55, 1.85, 0.62, 0.21, and 0.068 ng/µL human DNA.

The results are shown in FIG. 5. The results show that the extract comprised an amplifiable amount of DNA. The extract comprised approximately 1.8 ng/µL DNA.

This example demonstrates the effective extraction of nucleic acid using a device and method of the invention.

Example 2

This example investigates extraction of nucleic acid from a sample using a device and method of the invention.
1. Extraction Devices as shown in FIG. 1 comprising an inner heat shrink tube, a thermostatic valve and purification filter were used. The purification filter comprised 5 mg or 10 mg activated charcoal.

200 µL buffer comprising 5 mM Tris (pH 8.3 at 20° C.), 0.5% Triton X-100 and 4 µL prepGEM enzyme (ZyGEM Corporation Ltd, New Zealand) and 10 µl blood obtained from a finger-prick was added to the heat-shrink tube of each device.

The heat-shrink tube was sealed and then heated for 5 minutes at 75° C. and a further 2 minutes at 95° C. After 60 seconds at the higher temperature, the liquid flowed through the purification filter and from the device, and was collected in a tube. Approximately 130 µL of the extract was recovered.
2. Quantitative PCR Quantitative PCR using 5 µL samples of the extract or standards comprising known amounts of human DNA was conducted using the method described for Example 1.

Figure 6:
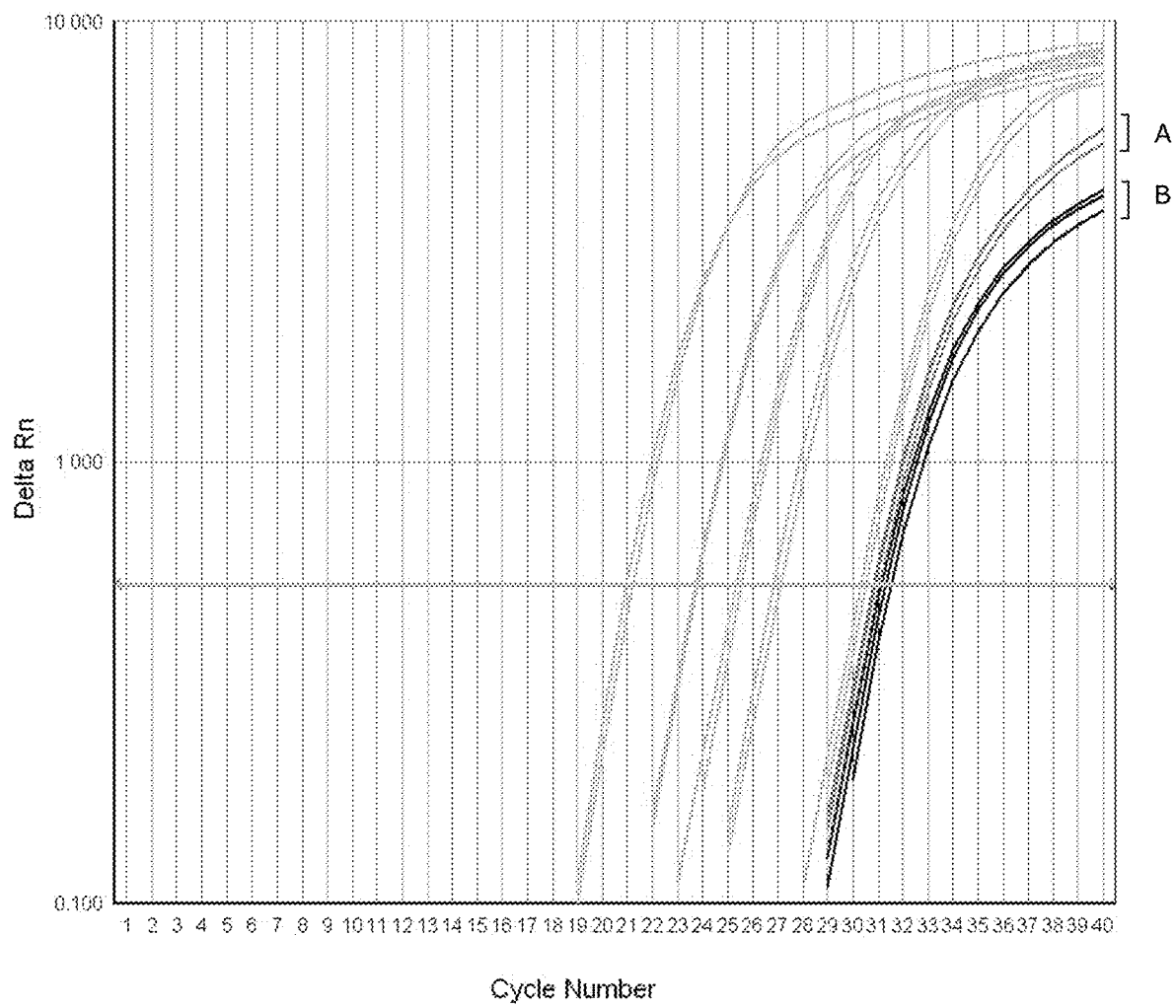
FIG. 6 shows the results of quantitative PCR of extracts obtained from a blood sample using a method and device of the invention. The plots show amplification of samples of the extract using a device comprising A) 10 mg activated charcoal, and B) 5 mg activated charcoal. The light grey plots, from left to right, show amplification of standards comprising: 5.55, 1.85, 0.62, 0.21, and 0.068 ng/µL human DNA.

The results are shown in FIG. 6. The results show that the extracts comprised an amplifiable amount of DNA. The extracts comprised approximately 70 pg/µL. The higher endpoint of the plot for the extract obtained from the device comprising 10 mg activated charcoal indicates that the amount of PCR inhibitors in the extract was reduced compared with the extract obtained from the device comprising 5 mg activated charcoal.

This example demonstrates the effective extraction of nucleic acid using a device and method of the invention.

INDUSTRIAL APPLICATION

The methods and devices of the invention have utility for a wide range of medical, agricultural, horticultural, environmental and other laboratory applications, including the extraction, separation or purification of biomolecules such as nucleic acids from samples for amplification, identification, analysis and diagnostics.

The invention claimed is:
1. A method for preparing a biomolecule-containing composition, the method comprising the steps of
   a) providing a device comprising a body at least partially formed of a heat-deformable material, the body defining
      i. an inner chamber, wherein, in a first configuration, the inner chamber has a volume sufficient to receive a sample comprising a biomolecule,
      ii. a first opening located at one end of the device to receive said sample into the inner chamber, and
      iii. a second opening located at or towards the opposing end of the device;
   b) adding a sample comprising a biomolecule to the inner chamber of said device, wherein the inner chamber comprises one or more reagents, or one or more reagents are added to the inner chamber, and wherein at least one of the sample and the one or more reagents comprises a liquid;

c) maintaining the device at a first temperature and for a duration sufficient to allow the one or more reagents to modify one or more substances in the sample to form a processed sample comprising the biomolecule, and d) maintaining the device at a second temperature and for a duration sufficient to deform the heat-deformable material such that the inner chamber adopts a second configuration having a chamber volume less than the chamber volume of the first configuration, thereby expelling at least a part of the processed sample through the second opening from the device, and e) thereby recovering the biomolecule-containing composition.

2. The method according to claim 1, wherein the one or more reagents comprises:
 a) an enzyme,
 b) a thermostable enzyme, a thermophilic enzyme, a mesophilic enzyme, or a proteolytic enzyme,
 c) an alkaline proteinase, a serine protease, a metalloproteinase, a neutral proteinase, a threonine proteinase, an aspartate proteinase, a cysteine proteinase, or a cell-wall degrading enzyme,
 d) a thermostable proteinase derived from a thermophilic *Bacillus* species, or
 e) cellulase, hemicellulase, pectinase, glucouronidase, glucanase, chitinase, laminarinase, lyticase, lysozyme, subtilisin, proteinase K, trypsin, *Bacillus* sp. EA1 proteinase, thermolysin, caldolysin, a *Thermus* proteinase, or a combination of any two or more thereof.

3. The method according to claim 1, wherein the second temperature is sufficient to inactivate the one or more reagents.

4. The method according to claim 1, further comprising an additional heating step between step c) and step d), or after step d), the additional heating step comprising maintaining the device at a temperature and for a duration sufficient to inactivate the one or more reagents.

5. The method according to claim 1, comprising maintaining the device:
 a) at a first temperature at which the inner chamber is not substantially deformed,
 b) at a first temperature of from about 65 to about 75° C.,
 c) at a first temperature for a period of from about 1 minute to about 5 minutes,
 d) at a second temperature of from about 85 to about 99° C., or
 e) at a second temperature for a period of from about 30 seconds to about 5 minutes.

6. The method according to claim 1, wherein the body is at least partially housed within an outer body.

* * * * *